United States Patent [19]

Lockhoff et al.

[11] Patent Number: 4,737,488
[45] Date of Patent: * Apr. 12, 1988

[54] IMMUNE SYSTEM-STIMULATING N-GLYCOSYLATED UREAS AND CARBAMATES

[75] Inventors: Oswald Lockhoff, Cologne; Bernd-Wieland Krüger, Wuppertal; Peter Stadler, Haan; Karl G. Metzger, Wuppertal, all of Fed. Rep. of Germany; Hans-Georg Opitz, Berkeley, Calif.; Klaus Schaller; Klaus G. Stünkel, both of Wuppertal, Fed. Rep. of Germany; Hans-Joachim Zeiler, Velbert, Fed. Rep. of Germany

[73] Assignee: Bayer Aktiengesellschaft, Leverkusen, Fed. Rep. of Germany

[ * ] Notice: The portion of the term of this patent subsequent to Mar. 4, 2003 has been disclaimed.

[21] Appl. No.: 676,160

[22] Filed: Nov. 29, 1984

[30] Foreign Application Priority Data

Dec. 14, 1983 [DE] Fed. Rep. of Germany ....... 3345250
Dec. 23, 1983 [DE] Fed. Rep. of Germany ....... 3346623

[51] Int. Cl.⁴ .................... A61K 31/70; C07H 5/06
[52] U.S. Cl. .................... 514/42; 536/18.7; 536/22; 536/53
[58] Field of Search ............. 536/22, 53; 514/42

[56] References Cited

U.S. PATENT DOCUMENTS

| | | | |
|---|---|---|---|
| 4,241,052 | 12/1980 | Tsujihara et al. | 536/22 |
| 4,241,053 | 12/1980 | Tsujihara et al. | 536/22 |
| 4,367,226 | 1/1983 | Foye | 536/22 |
| 4,574,122 | 3/1986 | Krüger et al. | 514/42 |

FOREIGN PATENT DOCUMENTS

| | | | |
|---|---|---|---|
| 0091645 | 10/1983 | European Pat. Off. | 536/22 |
| 0035067 | 3/1980 | Japan | 536/22 |

OTHER PUBLICATIONS c.f. Arzneimittel, Entwicklung Wirkung Darstellung, Band 5, Verlage Chemie, Weilheim, 1972, p. 345.
Chemical Abstracts, vol. 59, No. 13, Dec. 23, 1963.
Carbohydrate Research, 88 (1981) 61-75.

Primary Examiner—J. R. Brown
Assistant Examiner—Elli Peselev
Attorney, Agent, or Firm—Sprung Horn Kramer & Woods

[57] ABSTRACT

Compounds of the formula

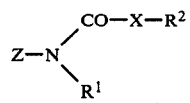

wherein
$R^1$ is hydrogen, an optionally substituted aromatic hydrocarbon radical, an aralkyl radical or an optionally substituted aliphatic hydrocarbon radical having up to 45 C atoms,
$R^2$ is an optionally substituted aromatic hydrocarbon radical, an aralkyl radical or an optionally substituted aliphatic hydrocarbon radical having 5-50 C atoms,
X is O, S, NH or NR, R being an alkyl radical having up to 20 C atoms, and
Z is a glycosyl radical bonded via the anomeric carbon atom, or pharmaceutically acceptable salts thereof stimulate the immune system.

20 Claims, No Drawings

IMMUNE SYSTEM-STIMULATING N-GLYCOSYLATED UREAS AND CARBAMATES

The present invention relates to new N-glycosylated ureas, carbamates and thiocarbamates, processes for their preparation and their use for influencing the body's own defences.

The new compounds correspond to the general formula I

wherein
- $R^1$ represents hydrogen, an optionally substituted aromatic hydrocarbon radical, an aralkyl radical or an optionally substituted, cyclic, straight-chain or branched, saturated or monounsaturated or polyunsaturated hydrocarbon radical having up to 45 C atoms,
- $R^2$ represents an optionally substituted aromatic hydrocarbon radical, an aralkyl radical or an optionally substituted, cyclic, straight-chain or branched, saturated or monounsaturated or polyunsaturated hydrocarbon radical having 5-50 C atoms,
- X represents O, S, NH or NR, R representing an alkyl radical having up to 20 C atoms, preferably up to 10 C atoms, and
- Z represents a glycosyl radical bonded via the anomeric carbon atom.

When $R^1$ denotes a hydrocarbon radical, it generally represents an alkyl, alkenyl, cycloalkyl, cycloalkenyl or aryl radical, it also being possible for these to occur together, for example as arylalkyl, alkylaryl, alkylcycloalkyl, arylcycloalkyl and the corresponding combinations with unsaturated alkyl and cycloalkyl moieties.

When the radical $R^1$ denotes alkyl or alkenyl, it is also possible for individual methylene or methyne groups, in general up to 5, preferably 1 or 2, to be interrupted by O, S or N. If the chain is interrupted by N, this nitrogen atom carries H, an alkyl radical having up to 20 carbon atoms or a CO-alkyl radical, this alkyl group having up to 20 C atoms, preferably up to 10 C atoms in each case.

$R^1$ preferably consists of a hydrocarbon radical having 7-21 C atoms.

It is very particularly preferred for $R^1$ to represent an alkyl or alkenyl radical having 7-21 C atoms.

Examples which may be mentioned of saturated radicals $R^1$ are: methyl, ethyl, n-propyl, i-propyl, n-butyl, i-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, eicosyl, docosyl, tetracosyl, triacontyl, ethylpentyl, methyldecyl, i-propyldecyl, methyltridecyl, pentylhexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl and 2-octadecyleicosyl.

Examples of unsaturated radicals are: ethenyl, prop-1-enyl, prop-2-enyl, i-butenyl, but-1-enyl, but-2-enyl, pent-1-enyl, pent-2-enyl, pent-3-enyl, pent-4-enyl, hex-1-enyl, hex-2-enyl, hex-3-enyl, hex-4-enyl, hex-5-enyl, dec-1-enyl, dec-5-enyl, dec-9-enyl, heptadec-2-enyl, buta-1,3-dienyl, penta-1,3-dienyl, penta-1,4-dienyl, heptadeca-8,11-dienyl and heptadeca-8,11,14-trienyl.

In general, the longer-chain unsaturated radicals are preferred, especially the monounsaturated or diunsaturated alkenyls having 7 to 21 carbon atoms.

The unsaturated hydrocarbon radicals can exist as pure cis or trans isomers or also as mixtures of isomers.

Examples of cyclic radicals are: cyclopropyl, cyclobutyl, cyclopentyl, cyclohexyl, cycloheptyl, adamantyl, cyclobutylcyclopentyl, cyclopentylcyclopentyl, cyclohexylcyclopentyl, cyclohexylcyclohexyl, cyclohexyladamantyl, adamantylcyclohexyl, dicyclohexylcyclopentyl and decahydronaphthyl.

Examples of alkylcycloalkyl and cycloalkyl-alkyl radicals which may be mentioned are: methylcyclopentyl, ethylcyclopentyl, n-propylcyclopentyl, i-propylcyclopentyl, butylcyclopentyl, octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexylhexyl, cyclohexyldecyl, cyclopentylcyclohexylethyl, cyclohexylcyclopentylethyl and cyclohexylcyclohexylethyl.

In the above examples where the cycloalkyl radicals are disubstituted, the substituents can have either a cis or trans arrangement relative to one another.

When $R^1$ denotes aryl, it preferably represents aromatic hydrocarbon radicals having 6, 10 or 12 carbon atoms. Examples of these are phenyl, biphenyl and naphthyl.

The aryl radicals can be substituted, preferably by hydroxy, $C_1$-$C_4$-alkyl, $C_1$-$C_4$-alkoxy, halogen, preferably F, Cl and Br, and nitro. If they are substituted, there are 1-3 or, in the case of halogen, 1-5 substituents. Examples of these substituted aryl radicals are: nitrophenyl, methoxyphenyl, chlorophenyl, dichlorophenyl, hydroxynaphthyl, methylphenyl, butylphenyl.

Examples in which the radicals $R^1$ in the formula (I) represent hydrocarbon radicals interrupted by oxygen, sulphur and/or nitrogen atoms are methoxyethyl, methoxyethoxyethyl, dimethylaminoethoxyethyl, dibutylaminohexyl and N-methylaminodecyl.

The radicals $R^1$ can be substituted, preferably by 1-3 substituents. Preferred substituents for these radicals are $C_6$-, $C_{10}$- or $C_{12}$-aryl, halogen, preferably Cl and Br, amino, $C_1$-$C_6$-alkylamino, di-$C_1$-$C_6$-alkylamino, oxo, OH, $C_1$-$C_6$-alkoxy, SH, $C_1$-$C_6$-alkylmercapto, $C_1$-$C_{20}$-alkyl-COO and $C_1$-$C_{20}$-alkyl-OC-NH.

Examples of radicals $R^1$ substituted in this way are mercaptoethyl, β-hydroxytridecyl, ω-hydroxyheptadecenyl, oxobutyl, aminodecyl, chloroethyl, fluoromethyl, ω-chlorododecyl, ω-fluorohexadecyl, ω-fluorooctadecyl, ω-chlorotetradecyl, ω-chlorohexadecyl, ω-chloroheptadecyl, ω-chlorooctadecyl, 2-aminododecyl, 2-aminohexadecyl, 2-aminooctadecyl, 2-(methylamino)tetradecyl, 2-(hexylamino)octadecyl, 2-(dimethylamino)hexadecyl, 2-oxotetradecyl, 4-oxotetradecyl, 2-oxoctadecyl, 2-hydroxytetradecyl, 2-hydroxyoctadecyl, 2-methoxyoctadecyl, 2-(hexyloxy)tetradecyl, 4-mercaptooctadecyl, 2-methylthiotetradecyl, 3-methylthiotetradecyl, 2-(acetyloxy)tetradecyl, 3-methylthiotetradecyl, 2-(acetyloxy)tetradecyl, 2-(lauroyloxy)tetradecyl, 2-(myristoyloxy)hexadecyl, 2-(acetylamido)tetradecyl, 2-(myristoylamido)tetradecyl and ω-(acetylamido)tetradecyl, benzyl, methoxybenzyl, phenylethyl, phenylhexyl, phenyldodecyl, p-methoxyphenylhexyl, naphthylbutyl.

Like the radical $R^1$, the hydrocarbon radical $R^2$ can be an alkyl, alkenyl, cycloalkyl, cycloalkenyl or aryl radical, it also being possible for these meanings to be combined with one another as already indicated for $R^1$. In the same way, as mentioned for $R^1$, the radical $R^2$ can be interrupted by O, S or NR.

Furthermore, $R^2$ can be substituted as indicated for $R^1$ in respect of the type and number of substituents.

$R^2$ preferably has 10 to 25 carbon atoms.

Examples of radicals $R^2$ are: n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, eicosyl, docosyl, tetracosyl, triacontyl, ethylpentyl, methyldecyl, i-propyldecyl, methyltridecyl, pentylhexadecyl, 1-dodecylhexadecyl, 2-dodecylhexadecyl, 3-dodecylhexadecyl, 1-hexadecyloctadecyl, 2-hexadecyloctadecyl, 3-hexadecyloctadecyl, 4-hexadecyloctadecyl, 1-octadecyleicosyl, 2-octadecyleicosyl, pent-1-enyl, pent-2-enyl, pent-3-enyl, pent-4-enyl, hex-1-enyl, hex-2-enyl, hex-3-enyl, hex-4-enyl, hex-5-enyl, dec-1-enyl, dec-5-enyl, dec-9-enyl, heptadec-2-enyl, penta-1,3-dienyl, penta-1,4-dienyl, heptadeca-8,11-dienyl, heptadeca-8,11,14-trienyl, cyclopentyl, cyclohexyl, cycloheptyl, adamantyl, cyclobutylcyclopentyl, cyclopentylcyclopentyl, cyclohexylcyclopentyl, cyclohexylcyclohexyl, cyclohexyladamantyl, adamantylcyclohexyl, dicyclohexylcyclopentyl, decahydronaphthyl, methylcyclopentyl, ethylcyclopentyl, n-propylcyclopentyl, i-propylcyclopentyl, butylcyclopentyl, octylcyclopentyl, methylcyclohexyl, ethylcyclohexyl, propylcyclohexyl, butylcyclohexyl, hexylcyclohexyl, decylcyclohexyl, cyclopentylmethyl, cyclopentylethyl, cyclopentylpropyl, cyclopentylbutyl, cyclopentylpentyl, cyclopentylhexyl, cyclopentyloctyl, cyclopentyldecyl, cyclohexylmethyl, cyclohexylethyl, cyclohexylpropyl, cyclohexylbutyl, cyclohexylhexyl, cyclohexyldecyl, cyclopentylcyclohexylethyl, cyclohexylcyclopentylethyl and cyclohexylcyclohexylethyl, phenyl, biphenyl, naphthyl, nitrophenyl, methoxyphenyl, chlorophenyl, dichlorophenyl, hydroxynaphthyl, benzyl, methoxybenzyl, phenylethyl, phenylhexyl, phenyldodecyl, p-methoxyphenylhexyl, naphthylbutyl, methoxyethoxyethyl, dimethylaminoethoxyethyl, dibutylaminohexyl, β-hydroxytridecyl, hydroxyheptadecenyl, aminodecyl, N-methylaminodecyl, N-octylaminododecyl, N-dihexylaminotetradecyl, β-acetyloxytridecyl, β-lauroyloxytridecyl, β-myristoyloxytridecyl, β-palmitoyloxytridecyl, β-stearoyloxytridecyl, β-myristoyloxypentadecyl, β-myristoyloxyheptadecyl, stearoylamidopentadecyl, acetylamidoheptadecyl, 2-(methylthio)tridecyl and 5-(propylthio)pentadecyl.

Z in the formula (I) denotes a glycosyl radical which, in the formulae according to the invention, is always bonded to the urethane, thiocarbamate or urea group via the anomeric carbon atom. According to the invention, the term "glycosyl radical" is to be understood as meaning monosaccharide, disaccharide and oligosaccharide radicals, preferably monosaccharides and disaccharides, in which, if appropriate, one or more hydroxyl groups are substituted by protecting groups customary in carbohydrate chemistry and chosen from the group comprising O-acyl, O-alkyl, O-alkylidene, O-silyl, O-stannyl and O-stannylidene, or one or more hydroxyl groups can be replaced with amino groups, acylamido groups, azido groups, nitro groups, thiol groups, lower alkoxy groups, hydrogen atoms or halogen atoms, and the glycosyl radicals can also be in the form of the corresponding uloses, ulose derivatives or uronic acids optionally substituted by the above functional groups, or in the form of uronic acid derivatives.

According to the invention, the glycosyl radicals Z in the formula (I) are preferably in the pyranosyl or furanosyl form, the particular monosaccharide, disaccharide or oligosaccharide radicals preferably being composed of pentoses, hexoses or heptoses.

Examples of monosaccharide radicals according to the invention are glucopyranosyl, galactopyranosyl, mannopyranosyl, glucofurnaosyl, ribofuranosyl, arabinopyranosyl, lyxopyranosyl or D-glycero-D-glucoheptopyranosyl radicals. Examples of disaccharide and oligosaccharide radicals which may be mentioned are maltosyl, maltotriosyl, maltotetraosyl, lactosyl, cellobiosyl, melibiosyl or 6-O-α- or β-ribofuranosyl)gluocopyranosyl radicals, that is to say carbohydrate systems which are composed of sugars having the same or different numbers of C atoms and in which the sugars can be in the pyranose and/or furanose form. The glycosidic bonds between the individual sugar units can be in the α and/or β form and the glycosidic linkage of the individual sugar units can be effected starting from an anomeric carbon atom, either via the primary OH group or via one of the secondary hydroxyl groups of the saccharide moiety functioning as an aglycon Examples which may be mentioned of monosaccharide, disaccharide and oligosaccharide radicals in which one or more OH groups are replaced with amino groups, acylamido groups, azido groups, hydrogen, nitro, thiol groups, lower alkoxy or halogen are 2-acetylamido-2-deoxyglucopyranosyl, 2-amino-2-deoxyglucopyranosyl, 2-caproylamido-2-deoxyglucopyranosyl, 2-lauroylamido-2-deoxyglucopyranosyl, 2-myristoylamido-2-deoxyglucopyranosyl, 2-palmitoylamido-2-deoxyglucopyranosyl, 2-stearoylamido-2-deoxyglucopyranosyl, 4-azido-4-deoxyglucopyranosyl, 4-stearoylamido-4-deoxyglucopyranosyl, 4-dodecoylamido-4-deoxyglucopyranosyl, 6-hexadecanoylamido-6-deoxyglucopyranosyl, 2,6-diamino-2,6-dideoxyglucopyranosyl, 6,6'-diamino-6,6'-dideoxy-2,6-dideoxylactosyl, 6-amino-6,6'-dideoxylactosyl, 6-deoxymannopyranosyl, 2-deoxyribofuranosyl, fucosyl, 5-fluoro-5-deoxyribofuranosyl, 6-O-methylglucopyranosyl, 6-deoxy-6-thioglucopyranosyl and 3-deoxy-3-nitrogalactopyranosyl.

If the glycosyl radicals are in the form of uronic acids or uronic acid derivatives, these are glycuronic acids with a free carboxyl group or with a carboxyl group esterified by alkyl, or glycuronamide derivatives with an unsubstituted or substituted nitrogen atom. Examples of corresponding sugars are galacturonic acid, methyl glucuronate or N-dodecylglucuronamide.

The compounds of the formula (I) contain several chiral C atoms and exist as pure optical diastereomers or as mixtures of diastereomers.

The compounds of the formula (I) according to the invention are thus carbamic acid, thiocarbamic acid or urea derivatives which, on the nitrogen atom substituted by the abovementioned radical $R^1$, additionally carry a simple or modified monosaccharide, disaccharide or oligosaccharide radical bonded in an N-glycosidic fashion, that is to say via the anomeric carbon atom.

The invention also relates to processes for the preparation of the compounds according to the formula (I). In these processes, a sugar, either in the free, i.e. unprotected, form or in the form of protected, optionally activated derivatives, is first reacted with an amino compound $R^1-NH_2$, either in the free form or in the form of a suitable acid addition salt, $R^1$ having the meaning described above.

The glycosylamines of the formula II $$Z-NH-R^1 \quad (II)$$

obtained in this way are then reacted in a second reaction step with, for example, halogenoformic acid esters of the formula III $$Y-CO-O-R^2 \quad (III).$$

In the formula (III), Y represents halogen, for example chlorine or bromine, and $R^2$ has the meaning given above. This process gives the urethanes according to the formula I, X representing oxygen in the formula I.

The reaction of the glycosylamines of the formula II, obtained in the first reaction step, with a thiocarbonic acid halide S-ester of the formula IV $$R^2-S-CO-Y \quad (IV)$$

in which Y represents halogen, for example chlorine, and $R^2$ has the meaning given above, leads to S-substituted thiocarbamates of the formula I, X representing a sulphur atom in the formula I.

If the glycosylamines of the formula II, obtained in the first reaction step, are reacted in the second reaction step with an organic isocyanate of the formula V $$R^2-NCO \quad (V)$$

$R^2$ having the meaning given above, ureas according to the formula I are obtained, X in this case representing NH in the formula I.

Ureas according to the formula I in which X represents NH or N-alkyl are obtained by reacting carbamates according to the formula I in which X=O and which have a preferably aromatic, in any case activating O-substituent, for example p-nitrophenyl, with primary amines $R^2-NH_2$ or with secondary amines $R^2-NH-$alkyl, in an aminolysis reaction, to give the urea.

The compounds of the formula I according to the invention which can be obtained in this way are then deblocked in the case where protecting groups had been used, and, if necessary, purified by chromatography, recrystallization, extraction or the like.

In a preferred embodiment of the process according to the invention, the unblocked sugar Z—OH, OH representing the anomeric hydroxyl group and Z having the meaning described in the formula I, is reacted, in a manner which is in itself known (cf. G. P. Ellis and J. Honeyman, Advances in Carbohydrate Chemistry 10, 95 (1955)), with one to ten equivalents of the particular amine $R^1-NH_2$, in a suitable solvent or without a solvent, if appropriate in the presence of a catalyst, at temperatures of between 0° C. and 80° C., and the particular glycosylamines of the formula II are usually obtained in high yields, after working up, as amorphous or crystalline solids or as viscous syrups.

To prepare the N-glycosylated carbamates according to the formula I in which X represents an oxygen atom, the glycosylamine according to the formula II is then reacted with 1 to 5 equivalents of a halogenoformic acid ester according to the formula III, preferably a chloroformic acid ester, the reaction being carried out in an organic or aqueous-organic solvent, at temperatures of between 0° C. and 50° C., if appropriate in the presence of an inorganic or organic base, and the reaction product being isolated in the usual manner after the reaction has ended.

To prepare the N-glycosylated and S-substituted thiocarbamates of the formula I in which X represents S, the glycosylamine of the formula II is reacted with 1 to 10 equivalents, preferably 1 to 3 equivalents, of the S-substituted thiocarbonic acid halide of the formula IV, in an organic solvent, the reaction temperature being between $-10°$ C. and $+50°$ C., preferably about 25° C., and the reaction being carried out, if appropriate, in the presence of an inorganic or organic base.

To prepare the N-glycosylated ureas according to the formula I in which X represents NH, the glycosylamine according to the formula II is reacted with 1 to 5 equivalents, preferably 1 to 2 equivalents, of an organic isocyanate according to the formula V. The reaction is preferably carried out in an inert organic solvent, at temperatures of between $-20°$ C. and 60° C., preferably at 20° C., if appropriate with the addition of a basic catalyst. If a catalyst is added, care must be taken to ensure that the conversion of the amine to the urea is not also accomplished by the reaction of any hydroxyl or thiol groups present with the isocyanate.

Another method for the preparation of the N-glycosylated ureas according to the formula I in which X represents NH or- in contrast to the above variant- represents N-alkyl consists in the aminolysis of N-glycosylcarbamates according to the formula I in which X=O, $R^2$ representing an activating ester radical, preferably phenyl or p-nitrophenyl. The aminolysis of the active carbamates is carried out by reaction with 1 to 10 equivalents, preferably 1 to 3 equivalents, of a primary amine $R^2-NH_2$ or a secondary amine $R^2-NH-$alkyl, in a suitable organic solvent, for example tetrahydrofuran, dioxane or N,N-dimethylformamide, at temperatures of between 0° C. and 120° C., preferably 10° C. to 50° C., if appropriate with the addition of inorganic or organic bases, for example potassium carbonate, triethylamine or pyridine.

In the case where one or more free amino groups are present in the carbohydrate radical Z, these are provided with an amino-protecting group in a manner which is in itself known, before the reaction with the amine $R^1-NH_2$.

Possible amino-protecting groups are those groups customarily used in sugar and peptide chemistry (see, for example, Houben-Weyl, Methoden der organischen Chemie (Methods of organic chemistry), Volume XV, Georg Thieme Verlag, Stuttgart, 1974), which on the one hand are stable under the given reaction conditions, but which on the other hand can be split off again so selectively, after the preparation of the particular N-glycoside and its subsequent reaction with the compounds of the formulae III, IV or V, that the desired end product of the formula I is obtained, that is to say without cleavage of the carbamate, thiocarbamate or urea groups contained in the end product of the formula I. Preferred examples are acyl groups of the type

B denoting trichloromethyl or trifluoromethyl, or of the type

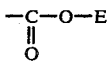

E representing, for example, ethyl, trichloroethyl, benzyl or tertiary butyl, or alternatively sulphenyl groups of the type

G representing phenyl, substituted phenyl, diphenyl- methyl or triphenylmethyl, and "substituted phenyl" denoting a phenyl radical which is substituted by one to three substituents from the group comprising nitro and lower alkyl or by 1 to 5 halogen atoms, preferably chlorine atoms. Examples which may be mentioned are the 2,4,5-trichlorophenylsulphenyl radical and the o-nitrophenylsulphenyl radical.

The introduction of these protecting groups into amino compounds and their subsequent cleavage to free the desired amino groups are known and are described, for example, in the literature reference cited above.

In another embodiment of the process for the preparation of products of the formula I in which one or more free amino groups are present in the glycosyl radical Z, the starting materials used are sugar derivatives Z—OH in which the amino group or the amino groups are initially in the form of azido radicals, that is to say in disguised form. In the final step of the preparation of the compounds of the formula I, these azido groups are reductively converted to amino groups in a manner which is in itself known, care being taken to ensure that the reducing agents used do not attack any other groups sensitive to reduction which may be present in the molecule.

Corresponding azido sugars and their preparation are known (see, for example, Methods in Carbohydrate Chemistry, Volume I, 242 to 246, Academic Press, 1962, New York and London). The reduction can be carried out using hydride donors, for example sodium borohydride or lithium aluminum hydride, catalytically activated hydrogen, triphenylphosphine in methanol-/ammonia/pyridine, or hydrogen sulphide or mercaptans in protic solvents.

All the common organic solvents can be used, preferably lower alkanols, but also water or aqueous alkanols.

The reactions are carried out, if appropriate, with the addition of organic acids, for example acetic acid, or inorganic acids, for example sulphuric acid, or with the addition of organic bases, for example pyridine, or inorganic bases, for example ammonia. The reactions are carried out at temperatures of between 0° and 120° C., preferably 10° C. to 40° C., if appropriate under elevated pressure and/or an inert gas.

In the case where, in the carbohydrate moiety Z of the end products of the formula I according to the invention, one or more OH groups are replaced with one or more acylamido groups, the sugars Z—OH are initially taken in the form of the corresponding acylamido sugars. The acylamido sugars are then reacted firstly, at the anomeric center, with the abovementioned amines to give the corresponding acylamidoglycosylamines, and in the second reaction step, at the C-1 amino group of the sugar moiety, with halogenocarbonic acid esters of the formula III, thiocarbonic acid chloride S-esters of the formula IV or isocyanates of the formula V to give, respectively, the N-(acylamidoalclosyl)carbamates, N-(acylamidoaldosyl)thiocarbamates or N-(acylamidoaldosyl)ureas according to the formula I.

Furthermore, the compounds of the formula I in which Z represents a sugar residue substituted by one or more acylamido groups can also be obtained by splitting off the temporary amino-protecting group, by the customary methods, from derivatives of the formula I in which Z initially represents an amino sugar blocked by one or more temporary amino-protecting groups of the previously described type

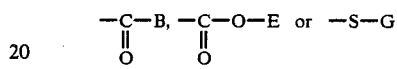

to give the corresponding N-(aminodeoxyglycosyl)urethanes, N-(aminodeoxyglycosyl)thiocarbamates or N-(aminodeoxyglycosyl)ureas according to the formula I, and then acylating the free amino group on the sugar ring, by the customary methods of organic chemistry, to give, respectively, N-(acylamidodeoxyglycosyl)urethanes, N-(acylamidodeoxyglycosyl)thiocarbamates or N-(acylamidodeoxyglycosyl)ureas.

The first process step in the preparation of the compounds of the formula I according to the invention is thus the reaction of a sugar Z—OH with an amine of the type $R^1$—$NH_2$ at the anomeric carbon atom to give the particular glycosylamine, water being split off.

Amines $R^1$—$NH_2$ which are liquid at room temperature can be reacted directly with the sugar, that is to say without a solvent. This reaction is carried out at temperatures of between 0° C. and 100° C., preferably at 25° C. to 70° C. Suitable catalysts are mineral acids, for example hydrochloric acid, sulphuric acid or nitric acid, or short-chain carboxylic acids such as acetic acid or propionic acid, and these are used in quantities of 0.001 to 0.05 equivalent.

It is possible in every case, and preferred in the case of amines $R^1$—$NH_2$ which are solid at room temperature, to prepare the glycosylamines in the presence of a solvent. The reaction is then preferably carried out in the presence of a diluent which is inert under the reaction conditions and which is preferably such that at least either the reactants or the reaction product are soluble therein.

Possible diluents are alcohols such as methanol, ethanol, propan-1-ol and propan-2-ol, ethers such as tetrahydrofuran or dioxane, and dimethylformamide, it being preferable to add water except in the case where alcohols are used. Moreover, water by itself is also a suitable solvent, preferably in the case of short-chain amines $R^1$—$NH_2$. It can also be advantageous to use alkanols mixed with water.

When using solvents in the preparation of the glycosylamines, the reaction temperatures are between −10° C. and 120° C., preferably between 30° C. and 70° C.

The particular diluent can be added before or during the reaction, as desired. In the case of long-chain amines $R^1$—$NH_2$, it is preferred to add the diluent before the reaction.

The glycosylamines prepared as described above crystallize either directly or after cooling and can be precipitated or crystallized by the addition of suitable co-solvents, preferably of low polarity, such as acetone, diethyl ether, cyclohexane, ethyl acetate or petroleum ether, if appropriate with cooling; any excess amine $R^1$—$NH_2$ present can be removed by washing or recrystallizing the product in a manner which is in itself known.

The second process step in the preparation of the compounds of the formula I according to the invention is the selective reaction of a glycosylamine of the formula II, obtained as described above, with formic acid derivatives of the formulae III, IV or V.

These formic acid derivatives are preferably reacted with the glycosylamines in the presence of a diluent in which the reactants are completely or only partially dissolved.

Possible diluents are organic or inorganic solvents, preferably those which reduce as far as possible, or prevent, secondary reactions under the reaction conditions. The reaction can also be carried out either in organic solvents such as ethers, for example tetrahydrofuran and dioxane, alcohols, for example ethanol and propanol, ketones, for example acetone or methyl ethyl ketone, dimethylformamide, ethyl acetate or pyridine, or in mixtures of these solvents with one another and/or with water. In general, it is preferred to use anhydrous solvents.

The reactions with the formic acid derivatives can be carried out in the presence of basic adjuvants. It is possible to use all the basic compounds customary in organic synthesis, for example tertiary aliphatic amines or aromatic amines or alkali metal and alkaline earth metal hydroxides or carbonates such as sodium hydroxide, sodium carbonate or calcium carbonate.

The carbamates, thiocarbamates or ureas obtained in this way are isolated, by processes which are in themselves known, in the form of crystalline or amorphous solids or as viscous syrups and, if necessary, are purified by recrystallization, chromatography, extraction or the like.

In the case of compounds containing protected amino groups in the glycosyl moiety, the protecting groups are split off in a manner which is in itself known.

The following reaction scheme is intended to illustrate, by way of example, one of the preferred embodiments of the preparation of compounds of the formula I according to the invention.

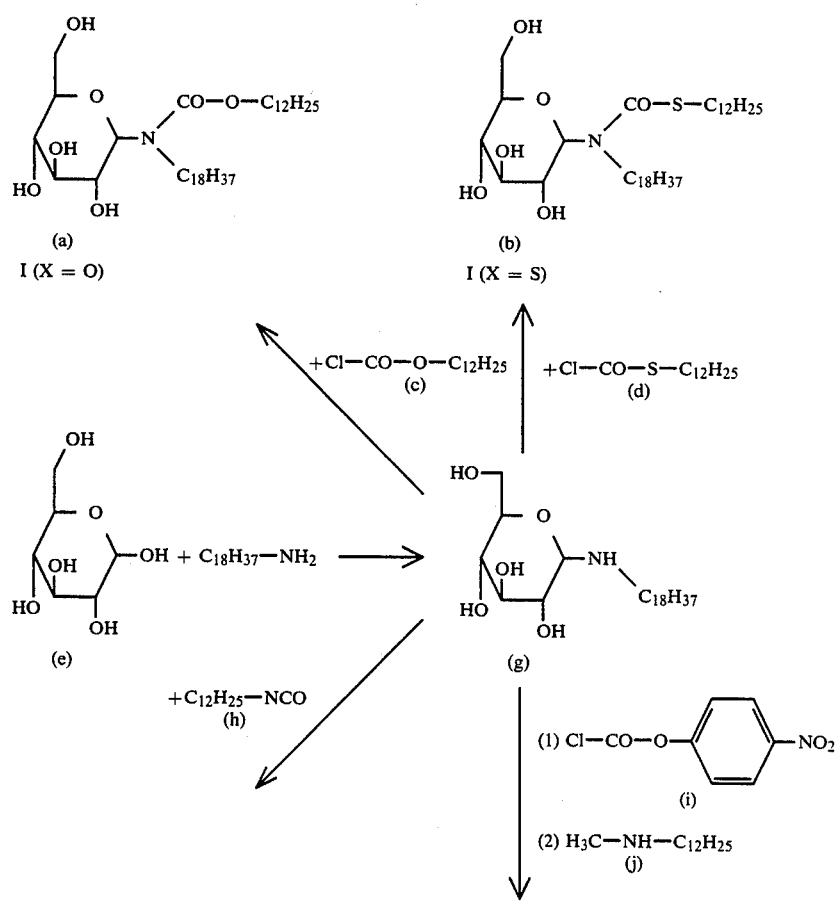

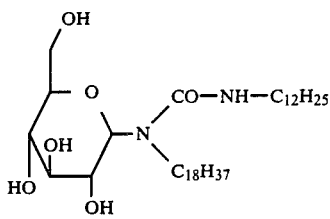

(k)

I (X = NH)

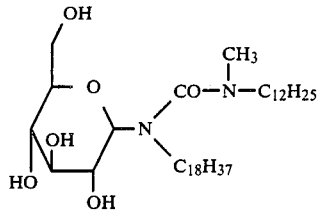

(l)

I (X = N—CH₃)

Glucose (e) is reacted with stearylamine (f) to give the glucosylamine (g). In the second reaction step, the glucosylamine (g) is reacted with dodecyl chloroformate (c) to give the carbamate (a) [=I (X=O)], or with the S-dodecyl ester of thiocarbonic acid chloride (d) to give the S-dodecyl thiocarbamate (b) [=I (X=S)], or with dodecyl isocyanate (h) to give the urea (k) [=I (X=NH)], or successively with p-nitrophenyl chloroformate (i) and N-methyl-N-dodecylamine (j) to give the urea (l) [=I (X=N—CH₃)].

The invention also relates to salts of the compounds of the formula I. These are primarily non-toxic salts which can usually be employed for pharmaceutical purposes, for example alkali metal or ammonium salts, chlorides or acetates.

The compounds of the invention have a pronounced defence-enhancing action. It has been found that the class of compounds increases the antibody synthesis of the immune system in an antigen-specific way and moreover enhances the unspecific defences peculiar to the host. These results were obtained by means of the following experimental procedures.

Increase in the primary humoral immunity in vitro towards sheep erythrocytes (SE).

It is possible experimentally to induce in vitro the development of a humoral immune response with heterologous red blood cells by primary immunization of mouse spleen cells in suspension cultures (R. I. Mishell and R. W. Dutton, J. Exp. Med. 126, 423 (1967)). For this purpose, Balb/c mouse spleen cells are cultured for 5 days in the presence of antigen (SE) and the test substance. The cells are harvested, washed and plated out together with the antigen and complement in semi-solid agar, and incubated at 37° C. for 2 hours (N. K. Jerne, A. A. Nordin and C. Henry, "Cell bound Antibodies", eds. Amos and Koprowski, Wistar Inst. Press, Philadelphia, USA, pp 109 (1963)). The antigen sensitization of mouse lymphocytes in the primary culture results in the synthesis and release of antibodies. The specific antibodies which are secreted bind to the SE antigen and lyze these cells due to the presence of the complement (plaque formation). Substances of the present class of compounds are capable of increasing the number of antibody-forming cells in a dose-dependent manner in the range 3–100 μg/ml (Table 1).

TABLE 1

Action of different selected N—glycosylated substances of the present class of compounds

| | Substance Antibody-secreting cells/culture as a function of the dose (μg/ml) | | | | |
|---|---|---|---|---|---|
| Example No. | 0 | 3 | 10 | 30 | 100 |
| 52 | 3915 | 2980 | 3340 | 3290 | 9150 |
| 28 | 4460 | 4850 | 6300 | 16760 | 18560 |
| 10 | 1590 | 2920 | 6480 | 7920 | 11880 |
| 9 | 1560 | 1020 | 1570 | 7940 | 9720 |
| 15 | 485 | 725 | 1830 | 1950 | 6480 |
| 11 | 1190 | 410 | 1020 | 3780 | 6080 |

Increase in the primary humoral immunity in vivo towards the soluble antigen ovalbumin.

NMRI mice were immunized subcutaneously (s.c.) with a suboptimal dose of antigen (1 μg/animal, day 0). When the antigenic stimulation was suboptimal, only a small number of lymphocytes in the animals were stimulated to synthesize antibodies. Additional treatment of the animals with compounds of the given examples of the present invention is capable of significantly increasing the antibody titre in the serum of the animals with a single subcutaneous administration of 10–30 mg/kg. The antibody titre is determined by indirect haemagglutination on day 10. The effect of the treatment is expressed by the geometric mean of log₂ of the titre.

The immunostimulant effect of the compounds mentioned is antigen-dependent, in contrast to other immunostimulants, for example bacterial immunostimulants, such as LPS from Gram-negative bacteria, that is to say the substances surprisingly induce antibody synthesis only when combined with an antigenic stimulus (in this case SE or ovalbumin). In contrast to the conventional immunostimulants mentioned, they have no mitogenic properties. Tolerability.

Although compounds of the type described display their potentiating effect on mice after, for example, a single dose of only 10 mg/kg, administered intraperitoneally or orally, no toxic effects are observed even on administration of 100 mg/kg. Thus, the substances mentioned have good tolerability.

The compounds according to the invention have the capability on the one hand of increasing the immunogenicity of an antigen when mixed therewith, and on the other hand of increasing the immunological responsiveness of the treated organism on systemic administration. At the same time, the said substances are capable of activating the lymphocytes responsible for the formation of antibodies.

The new compounds can thus be used as adjuvants mixed with vaccines for the purpose of improving the success of vaccination and increasing the protection from infection provided by the immunity to bacterial, viral or parasitic pathogens.

Moreover, when mixed with a wide variety of antigens, the compounds described are suitable as adjuvants for the experimental and industrial production of antisera for therapy and diagnosis.

Furthermore, the new compounds can be used, even without simultaneous administration of antigen, for promoting defence responses which are already taking place at a subthreshold level in humans and animals. Accordingly, the compounds are particularly suitable for stimulation of the body's own defences, for example where there are chronic and acute infections or selective (antigen-specific) immunological deficiencies, and where there are congenital as well as acquired general (that is to say not antigen-specific) states of immunological deficiency such as occur in the elderly, during the course of severe primary diseases and, in particular, following therapy with ionizing radiation or with compounds having an immunosuppressive action. The compounds mentioned can thus preferably be administered also in combination with anti-infectious antibiotics, chemotherapeutic agents or other remedial procedures in order to counteract immunological damage. Finally, the compounds described are also suitable for the general prophylaxis of infectious diseases in humans and animals.

The compounds according to the invention increase the survival rate in the animal model of systemic candidiasis in mice and of acute bacterial infection.

Description of the experiment

Mice of the SPD-CFW 1 type were infected intravenously with $2-6 \times 10^5$ logarithmically growing cells of Candida albicans, suspended in physiological saline solution. Starting from day 3 after infection, the first symptoms of disease are recognizable in untreated control animals. Up to day 5, the first animals die of acute renal failure, and up to day 14 after infection, as a rule more than 80% of the untreated animals have died. In this test, the compounds according to the invention are effective in retarding disease. A significant disease-retarding action was achieved when, for example, the substance according to Example 24 was administered intraperitoneally (i.p.), in each case in a single dose 24 hours before infection, in concentrations of 1–50 mg/kg of body weight.

In the case of treated animals, a statistically significant increase was observed in the survival time, compared with the untreated control animals. Approximately 50% of the treated animals survived an observation period of 14 days, compared with approximately 20% of untreated control animals.

The compounds according to the invention can be used by themselves as prophylactic agents for combating existing infections, or in combination with antibiotic therapy for increasing the therapeutic effect of antibiotics and chemotherapeutic agents (for example penicillins, cephalosporins, aminoglycosides and the like) in infected humans and animals.

It has been found that therapy of infections caused in mice by pathogenic germs which lead to the death of the experimental animals within 24–48 hours is possible by prophylactic treatment—preferably intraperitoneally—with 1–80 mg/kg of the compounds according to the invention. This applies to a large number of Gram-positive pathogens (for example Staphylococci) and Gram-negative pathogens (for example E. coli, Klebsiella, Proteus and Pseudomonas). This list is given as an example and is not to be interpreted as in any way restrictive. Thus, for example, 40–100% of mice which have been infected with the pathogenic strain Klebsiella 63 survive this infection after treatment (for example 18 hours before infection) with 10–40 mg/kg of the compound of the invention according to Example 12, 13, 19, 22 or 24, while only 0 to 30% of the untreated control animals survived.

In another experimental model, it was shown that the therapeutic efficacy of antibiotics can be increased by the compounds according to the invention. Thus, mice were infected with the strain Pseudomonas W. This infection leads to the death of most of the control animals within 24 hours. Another group was treated with 4 mg/kg of sisomicin 30 hours after infection. It was shown that it was possible to make a decisive improvement in the therapeutic efficacy of the sisomicin in the experimental group which had been treated with the compounds according to the invention (examples cf. above) 18 hours before infection.

The pharmaceutical preparations of the present invention are preferably tablets or gelatine capsules which contain the active compounds together with diluents, for example lactose, dextrose, sucrose, mannitol, sorbitol or cellulose, and/or lubricants, for example diatomaceous earth, talc, stearic acid or salts thereof, such as magnesium stearate or calcuim stearate, and/or polyethylene glycol. Tablets additionally contain binders, for example magnesium aluminum silicate, starches such as corn, wheat, rice or arrowroot starch, gelatine, traganth, methylcellulose, sodium carboxymethylcellulose and/or polyvinylpyrrolidone, and, if desired, disintegrants, for example starches, agar, alginic acid or a salt thereof, such as sodium alginate, and/or effervescent mixtures, or adsorbents, colorants, flavorings and sweeteners. Injectable preparations are preferably isotonic aqueous solutions or suspensions. Suppositories, ointments or creams are primarily fatty emulsions or suspensions. The pharmaceutical preparations can be sterilized and/or contain adjuvants, for example preservatives, stabilizers, wetting and/or emulsifying agents, solubilizers, salts to control the osmotic pressure, and/or buffers. The present pharmaceutical preparations, which, if desired, can contain other compounds of pharmacological value, are produced in a manner which is in itself known, for example by conventional mixing, granulating or coating processes, and they contain from about 0.1% to about 75%, in particular from about 1% to 50%, of the active compounds mentioned.

The preparations of the present invention for oral administration can also be provided with a coating which is resistant to gastric juice.

The compounds according to the invention can be used as agents for increasing the defenses and as immunopotentiating agents for the treatment of chronic and acute infections (for example bacterial, viral and parasitic) and malignant tumors. Likewise, they can be used as adjuvants for vaccination, for the stimulation of phagocytosis and where there is dysregulation of the defense and immune systems.

EXAMPLES

Example 1

N-(D-Glucopyranosyl)dodecylamine 18 g of D-glucose are stirred in 50 ml of ethanol at 70° C., 18.5 g of dodecylamine are then added, heating is continued until the solution is clear, the mixture is left to cool to room temperature and the precipitated crystals are filtered off with suction for a further 20 hours. They are washed with ethanol and ether and dried in vacuo.

Elementary analysis: calculated: C 62.2%; H 10.6%; N 4.0%; found: C 62.2%; H 10.6%; N 4.2%

Example 2

N-(D-Glucopyranosyl)octadecylamine

The preparation is analogous to Example 1, starting from 11 g of glucose and 20 g of octadecylamine.

Elementary analysis: calculated: C 66.8%; H 11.4%; N 3.2%; found: C 66.9%; H 11.1%; N 3.4%

Example 3

N-(D-Galactopyranosyl)tetradecylamine

The preparation is analogous to Example 1, starting from 18 g of galactose and 20 g of tetradecylamine.

Elementary analysis: calculated: C 64.0%; H 10.9%; N 3.7%; found: C 64.1%; H 11.0%; N 3.8%

Example 4

N-(D-Galactopyranosyl)octadecylamine

The preparation is analogous to Example 1, starting from 11 g of galactose and 20 g of octadecylamine.

Elementary analysis: calculated: C 66.8%; H 11.4%; N 3.2%; found: C 66.9%; H 11.2%; N 3.4%

Example 5

N-(D-Mannopyranosyl)dodecylamine

The preparation is analogous to Example 1, starting from 18 g of mannose and 19 g of dodecylamine.

Elementary analysis: calculated: C 62.2%; H 10.7%; N 4.0%; found: C 62.3%; H 10.8%; N 4.2%

Example 6

N-(D-Mannopyranosyl)octadecylamine

The preparation is analogous to Example 1, starting from 22 g of mannose and 40 g of octadecylamine.

Elementary analysis: calculated: C 66.8%; H 11.4%; N 3.2%; found: C 66.9%; H 11.2%; N 3.1%

Example 7

N-(D-Ribopyranosyl)dodecylamine

The preparation is analogous to Example 1, starting from 15 g of D-ribose and 18 g of dodecylamine.

Elementary analysis: calculated: C 64.4%; H 11.0%; N 4.4%; found: C 64.4%; H 11.2%; N 4.6%

Example 8

N-(2-Acetamido-2-deoxy-D-glucopyranosyl)dodecylamine 15 g of N-acetylglucosamine and 19 g of dodecylamine are heated at 80° C. for 3 hours in 50 ml of ethanol, with stirring. The undissolved material is then filtered off hot, the filtrate is cooled and the precipitated product is filtered off with suction and rinsed with ethanol and ether. The residue on the filter is dried in vacuo.

Elementary analysis: calculated: C 61.9%; H 10.3%; N 7.2%; found: C 62.1%; H 10.3%; N 7.4%

Example 9

N-(D-Glucopyranosyl)-N-dodecyl-dodecylurethane 7.0 g of the compound of Example 1 are suspended in 50 ml of tetrahydrofuran and stirred with 10 g of potassium carbonate. 6.7 g of dodecyl chloroformate are added and stirring is continued until the reaction has ended (monitoring by thin layer chromatography). The reaction mixture is diluted with 50 ml of tetrahydrofuran and filtered, the filtrate is evaporated and the residue is purified by column chromatography (eluent toluene isopropanol 10:1).

$\alpha_D = 4.7°$ (c=1.0 in tetrahydrofuran)

Example 10

N-(D-Glucopyranosyl)-N-dodecyl-tetradecylurethane

The preparation is analogous to Example 9, starting from 7.0 g of the compound of Example 1 and 7.4 g of tetradecyl chloroformate.

$\alpha_D = 4.5°$ (c=0.95 in tetrahydrofuran)

Example 11

N-(D-Glucopyranosyl)-N-dodecyl-pentadecylurethane

The preparation is analogous to Example 9, starting from 7.0 g of the compound of Example 1 and 7.8 g of pentadecyl chloroformate.

$\alpha_D = 4.5°$ (c=1.1 in tetrahydrofuran)

Example 12

N-(D-Glucopyranosyl)-N-dodecyl-octadecylurethane

The preparation is analogous to Example 9, starting from 7.0 g of the compound of Example 1 and 8.9 g of octadecyl chloroformate.

Example 13

N-(D-Glucopyranosyl)-N-octadecyl-decylurethane

The preparation is analogous to Example 9, starting from 8.6 g of the compound of Example 2 and 5.9 g of decyl chloroformate.

$\alpha_D = 3.9°$ (c=1.01 in tetrahydrofuran)

Example 14

N-(D-Glucopyranosyl)-N-octadecyl-dodecylurethane

The preparation is analogous to Example 9, starting from 8.6 g of the compound of Example 2 and 6.7 g of dodecyl chloroformate.

$\alpha_D = 4.0°$ (c=1.4 in tetrahydrofuran)

Example 15

N-(D-Glucopyranosyl)-N-octadecyl-tetradecylurethane

The preparation is analogous to Example 9, starting from 8.6 g of the compound of Example 2 and 7.4 g of tetradecyl chloroformate.

Example 16

N-(D-Glucopyranosyl)-N-octadecyl-pentadecylurethane

The preparation is analogous to Example 9, starting from 8.6 g of the compound of Example 2 and 7.8 g of pentadecyl chloroformate.

Example 17

N-(D-Glucopyranosyl)-N-octadecyl-octadecylurethane

The preparation is analogous to Example 9, starting from 8.6 g of the compound of Example 2 and 8.9 g of octadecyl chloroformate.

Example 18

N-(D-Glucopyranosyl)-N-octadecyl(ethoxy-ethoxyethyl)urethane

The preparation is analogous to Example 9, starting from 8.6 g of the compound of Example 2 and 5.8 g of ethoxy-ethoxyethyl chloroformate.

Example 19

N-(D-Glucopyranosyl)-N-octadecyl(octylthioethyl)urethane

The preparation is analogous to Example 9, starting from 8.6 g of the compound of Example 2 and 6.8 g of octylthioethyl chloroformate.

Example 20

N-(D-Glucopyranosyl)-N-octadecyl(ethoxythiocarbonylthioethyl)urethane

The preparation is analogous to Example 9, starting from 8.6 g of the compound of Example 2 and 9 g of ethoxythiocarbonylthioethyl chloroformate.

Example 21

N-(D-Glucopyranosyl)-N-dodecyl(4-tert.-butylcyclohexyl)urethane

The preparation is analogous to Example 9, starting from 7.0 g of the compound of Example 1 and 5.9 g of 4-tert.-butylcyclohexyl chloroformate.

Example 22

N-(D-Glucopyranosyl)-N-dodecyl(4-(1,1,3,3-tetramethylbutyl)cyclohexyl)urethane

The preparation is analogous to Example 9, starting from 7.0 g of the compound of Example 1 and 7.4 g of 4-(1,1,3,3-tetramethylbutyl)cyclohexyl chloroformate.

Example 23

N-(D-Glucopyranosyl)-N-octadecyl(4-tert.-butylcyclohexyl)urethane

The preparation is analogous to Example 9, starting from 8.6 g of the compound of Example 2 and 5.9 g of 4-tert.-butylcyclohexyl chloroformate.

Example 24

N-(D-Glucopyranosyl)-N-octadecyl(4-(1,1,3,3,-tetramethylbutyl)cyclohexyl)urethane The prepration is analogous to Example 9, starting from 8.6 g of the compound of Example 2 and 7.4 g of 4-(1,1,3,3-tetramethylbutyl)cyclohexyl chloroformate.

Example 25

N-(D-Galactopyranosyl)-N-tetradecyl-octadecylurethane

The preparation is analgous to Example 9, starting from 7.5 g of the compound of Example 3 and 8.9 g of octadecyl chloroformate.

Example 26

N-(D-Galactopyranosyl)-N-octadecyl-dodecylurethane

The preparation is analogous to Example 9, starting from 8.6 g of the compound of Example 4 and 6.7 g of dodecyl chloroformate.

Example 27

N-(D-Galactopyranosyl)-N-octadecyl-octadecylurethane

The preparation is analogous to Example 9, starting from 8.6 g of the compound of Example 4 and 8.9 g of octadecyl chloroformate.

Example 28

N-(D-Galactopyranosyl)-N-octadecyl(4-tert.-butylcyclohexyl)urethane

The preparation is analogous to Example 9, starting from 8.6 g of the compound of Example 4 and 5.9 g of 4-tert.-butylcyclohexyl chloroformate.

Example 29

N-(D-Mannopyranosyl)-N-dodecyl-octadecylurethane

The preparation is analogous to Example 9, starting from 7.0 g of the compound of Example 5 and 8.9 g of octadecyl chloroformate.

Example 30

N-(D-Mannopyranosyl)-N-octadecyl-dodecylurethane

The preparation is analogous to Example 9, starting from 8.6 g of the compound of Example 6 and 6.7 g of dodecyl chloroformate.

Example 31

N-(D-Mannopyranosyl)-N-octadecyl-tetradecylurethane

The preparation is analogous to Example 9, starting from 8.6 g of the compound of Example 6 and 7.4 g of tetradecyl chloroformate.

Example 32

N-(D-Mannopyranosyl)-N-dodecyl(4-tert.-butylcyclohexyl)urethane

The preparation is analogous to Example 9, starting from 7.0 g of the compound of Example 5 and 5.9 g of 4-tert.-butylcyclohexyl chloroformate.

Example 33

N-(D-Mannopyranosyl)-N-octadecyl(4-(1,1,3,3-tetramethylbutyl)cyclohexyl)urethane The preparation is analogous to Example 9, starting from 8.6 g of the compound of Example 6 and 5.9 g of 4-(1,1,3,3-tetramethylbutyl)cyclohexyl chloroformate.

Example 34

N-(D-Glucopyranosyl)-N-dodecyl(1-undecylnonadecyl)urethane

The preparation is analogous to Example 9, starting from 7.0 g of the compound of Example 1 and 13.8 g of 1-undecylnonadecyl chloroformate.

Example 35

N-(D-Glucopyranosyl)-N-octadecyl(1-undecylnondecyl)urethane

The preparation is analogous to Example 9, starting from 8.6 g of the compound of Example 2 and 13.8 g of 1-undecylnondecyl chloroformate.

Example 36

N-(D-Ribopyranosyl)-N-dodecylurethane

The preparation is analogous to Example 9, starting from 6.4 g of the compound of Example 7 and 6.7 g of dodecyl chloroformate.

Example 37

N-(D-Ribopyranosyl)-N-dodecyl-octadecylurethane

The preparation is analogous to Example 9, starting from 6.4 g of the compound of Example 7 and 8.9 g of octadecyl chloroformate.

Example 38

N-(D-Ribopyranosyl)-N-dodecyl(4-tert.-butylcyclohexyl)urethane

The preparation is analogous to Example 9, starting from 6.4 g of the compound of Example 7 and 5.9 g of 4-tert.-butylcyclohexyl chloroformate.

Example 39

N-(2-Acetamido-2-deoxy-D-glucopyranosyl)-N-dodecyldodecylurethane

The preparation is analogous to Example 9, starting from 7.8 g of the compound of Example 8 and 6.7 g of dodecyl chloroformate.

Example 40

N-(2-Acetamido-2-deoxy-D-glucopyranosyl)-N-dodecyl-tetradecylurethane

The prepration is analogous to Example 9, starting from 7.8 g of the compound of Example 8 and 7.4 g of tetradecyl chloroformate.

Example 41

N-(2-Acetamido-2-deoxy-D-glucopyranosyl)-N-dodecyl(ethoxy-ethoxyethyl)urethane

The preparation is analogous to Example 9, starting from 7.8 g of the compound of Example 8 and 5.8 g of ethoxy-ethoxyethyl chloroformate.

Example 42

N-(D-Glucopyranosyl)-N-dodecyl-N'-dodecylurea 7.0 g of the compound of Example 1 are suspended in 150 ml of methanol. A solution of 4.2 g of dodecyl isocyanate in 20 ml of tetrahydrofuran is added dropwise. After about 4 hours, the mixture is evaporated in vacuo and the residue is purified by column chromatography (eluent methylene chloride/methanol 15:1).

$\alpha_D = 13.4°$ (c = 1.11 in tetrahydrofuran)

Example 43

N-(D-Glucopyranosyl)-N-dodecyl-N'-tetradecylurea

The preparation is analogous to Example 42, starting from 7.0 g of the compound of Example 1 and 4.8 g of tetradecyl isocyanate.

Example 44

N-(D-Glucopyranosyl)-N-dodecyl-N'-octadecylurea

The preparation is analogous to Example 42, starting from 7.0 g of the compound of Example 1 and 5.9 g of octadecyl isocyanate.

$\alpha_D = 13.2°$ (c = 0.97 in tetrahydrofuran)

Example 45

N-(D-Glucopyranosyl)-N-octadecyl-N'-tetradecylurea

The preparation is analogous to Example 42, starting from 8.6 g of the compound of Example 2 and 4.8 g of tetradecyl isocyanate.

Example 46

N-(D-Glucopyranosyl)-N-octadecyl-N'-(methoxyethoxyethyl)urea

The preparation is analogous to Example 42, starting from 8.6 g of the compound of Example 2 and 2.9 g of methoxyethoxyethyl isocyanate.

Example 47

N-(D-Glucopyranosyl)-N-dodecyl(4-nitrophenyl)urethane

The preparation is analogous to Example 9, starting from 17.4 g of the compound of Example 1 and 10.1 g of 4-nitrophenyl chloroformate.

Example 48

N-(D-Glucopyranosyl)-N-dodecyl-N'-methyl-N'-octadecylurea 3.1 g of the compound of Example 47 are dissolved in 50 ml of dimethylformamide and treated with 5.0 g of potassium carbonate. 1.8 g of N-methyloctadecylamine are added and the mixture is heated to 50° C. After the reaction has ended, the mixture is cooled to room temperature and filtered, the filtrate is evaporated in vacuo and the residue is purified by column chromatography (eluent toluene/isopropanol 10:1).

$\alpha_D = 8.5°$ (c = 1 in tetrahydrofuran)

Example 49

N-(D-Glucopyranosyl)-N-dodecyl-S-octadecylthiocarbamate 7.0 g of the compound of Example 1 are suspended in 100 ml of tetrahydrofuran and treated with 1.1 g of triethylamine. 7.0 g of the S-octadecyl ester of thiocarbonic acid chloride are added. After the reaction has ended, the mixture is subsequently stirred for 1 hour with 100 ml of methanol/triethylamine 1:1 and filtered and the filtrate is concentrated in vacuo. The residue is purified by column chromatography (eluent toluene/isopropanol 10:1).

$\alpha_D = +8.6°$ (c = 1.05 in tetrahydrofuran)

Example 50

N-(D-Glucopyranosyl)-N-octadecyl-S-octylthiocarbamate

The preparation is analogous to Example 49, starting from 8.6 g of the compound of Example 2 and 4.2 g of the S-octyl ester of thiocarbonic acid chloride.

$\alpha_D = 6.7°$ (c = 0.83 in tetrahydrofuran)

Example 51

N-(D-Glucopyranosyl)-N-octadecyl-S-octadecylthiocarbamate

The preparation is analogous to Example 49, starting from 8.6 g of the compound of Example 2 and 7.0 g of the S-octadecyl ester of thiocarbonic acid chloride.
$\alpha_D = 5.6°$ (c = 1.0 in tetrahydrofuran)

Example 52

N-(D-Glucopyranosyl)-N-octadecyl-N'-(3-trifluoromethylphenyl)urea

The preparation is analogous to Example 42, starting from 8.6 g of the compound of Example 2 and 3.8 g of m-trifluoromethylphenyl isocyanate.

It is understood that the specification and examples are illustrative but not limitative of the present invention and that other embodiments within the spirit and scope of the invention will suggest themselves to those skilled in the art.

We claim:

1. A compound of the formula

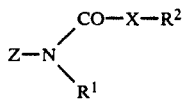

wherein
- $R^1$ is an aromatic hydrocarbon radical having 6, 10 or 12 carbon atoms; an aromatic hydrocarbon radical having 6, 10 or 12 carbon atoms and substituted by hydroxy, $C_1$–$C_4$-alkyl, $C_1$–$C_4$-alkoxy, halogen or nitro; an aliphatic hydrocarbon radical having 7 to 21 carbon atoms; or an aliphatic hydrocarbon radical having 7 to 21 carbon atoms and substituted by $C_6$-, $C_{10}$- or $C_{12}$-aryl, halogen, amino, $C_1$–$C_6$-alkylamino, di-$C_1$–$C_6$-alkyl-amino, oxo, OH, $C_1$–$C_6$-alkoxy, SH, $C_1$–$C_6$-alkyl-mercapto, $C_1$–$C_{20}$-alkyl-COO or $C_1$–$C_{20}$-alkyl-OC-NH,
- $R^2$ is an aromatic hydrocarbon radical having 6, 10 or 12 carbon atoms, or an aliphatic hydrocarbon radical having 7 to 21 carbon atoms and substituted by hydroxy, $C_1$–$C_4$-alkyl, $C_1$–$C_4$-alkoxy, halogen or nitro, or an aliphatic hydrocarbon radical having 10 to 25 carbon atoms, or an aliphatic hydrocarbon radical having 10 to 25 carbon atoms and substituted by $C_6$-, $C_{10}$- or $C_{12}$-aryl, halogen, amino, $C_1$–$C_6$-alkylamino, di-$C_1$–$C_6$-alkyl-amino, oxo, OH, $C_1$–$C_6$-alkoxy, SH, $C_1$–$C_{20}$-alkyl-OC-NH,
- X is O, S, NH or NR, R being an alkyl radical having up to 20 C atoms, and
- Z is a pyranosyl or furanosyl form of a mono-saccharide, disaccharide or oligosaccharide radical composed of pentoses, hexoses and heptoses, or a pharmaceutically acceptable salt thereof.

2. A compound according to claim 1, in which $R^1$ has up to 21 C atoms.

3. A compound according to claim 1, in which $R^2$ has 5 to 21 C atoms.

4. A compound according to claim 1, in which Z is a monosaccharide or oligosaccharide radical.

5. A compound according to claim 1, wherein such compound in N-(D-glucopyranosyl)-N-dodecyl-dodecylurethane or a pharmaceutically acceptable salt thereof.

6. A compound according to claim 1, wherein such compound is N-(D-glucopyranosyl)-N-dodecyl pentadecylurethane or a pharmaceutically acceptable salt thereof.

7. A compound according to claim 1, wherein such compound is N-(D-glucopyranosyl)-N-octadecyl-decylurethane or a pharmaceutically acceptable salt thereof.

8. A compound according to claim 1, wherein such compound is N-(D-glucopyranosyl)-N-octadecyl-dodecylurethane or a pharmaceutically acceptable salt thereof.

9. A compound according to claim 1, wherein such compound is N-(D-glucopyranosyl)-N-octadecyl(octylthioethyl)urethane or a pharmaceutically acceptable salt thereof.

10. A compound according to claim 1, wherein such compound is N-(D-glucopyranosyl)-N-dodecyl(4-(1,1,3,3-tetramethylbutyl)-cyclohexyl)urethane or a pharmaceutically acceptable salt thereof.

11. A compound according to claim 1, wherein such compound is N-(D-glucopyranosyl)-N-octadecyl(4-tert.-butylcyclohexyl)-urethane or a pharmaceutically acceptable salt thereof.

12. A compound according to claim 1, wherein such compound is N-(D-glucopyranosyl)-N-octadecyl(4-(1,1,3,3-tetramethylbutyl)-cyclohexyl)urethane or a pharamcutically acceptable salt thereof.

13. A compound according to claim 1, wherein such compound is N-(D-galactopyranosyl)-N-octadecyl(4-tert.-butylcyclohexyl)urethane or a pharmaceutically acceptable salt thereof.

14. A compound according to claim 1, wherein such compound is N-(D-glucopyranosyl)-N-dodecyl-N'-dodecylurea or a pharmaceutically acceptable salt thereof.

15. A compound according to claim 1, wherein such compound is N-(D-glucopyranosyl)-N-dodecyl-N'-octadecylurea or a pharmaceutically acceptable salt thereof.

16. A compound according to claim 1, wherein such compound is N-(D-glucopyranosyl)-N-dodecyl-N'-methyl-N'-octadecylurea or a pharmaceutically acceptable salt thereof.

17. An immune system-stimulating composition comprising an immune system-stimulating effective amount of a compound or salt according to claim 1 in admixture with a diluent.

18. A unit dose of a composition according to claim 17 in the form of a tablet, capsule or ampule.

19. A method of stimulating the immune system of a patient which comprises administering to such patient an immune system-stimulating effective amount of a compound or salt according to claim 1.

20. The method according to claim 19, wherein such compound is
N-(D-glucopyranosyl)-N-dodecyl-dodecylurethane,
N-(D-glucopyranosyl)-N-dodecyl-pentadecylurethane,
N-(D-glucopyranosyl)-N-octadecyl-decylurethane,
N-(D-glucopyranosyl)-N-octadecyl-dodecylurethane,
N-(D-glucopyranosyl)-N-octadecyl(octylthioethyl)urethane,
N-(D-glucopyranosyl)-N-dodecyl(4-(1,1,3,3-tetramethylbutyl)-cyclohexyl)urethane,
N-(D-glucopyranosyl)-N-octadecyl(4-tert.-butylcyclohexyl)-urethane,
N-(D-glucopyranosyl)-N-octadecyl(4-(1,1,3,3-getramethylbutyl)-cyclohexyl)urethane,
N-(D-galactopyranosyl)-N-octadecyl(4-tert.-butylcyclohexyl)urethane,
N-(D-glucopyranosyl)-N-dodecyl-N'-dodecylurea,
N-(D-glucopyranosyl)-N-dodecyl-N'-octadecylurea or
N-(D-glucopyranosyl)-N-dodecyl-N'-methyl-N'-octadecylurea,
or a pharmaceutically acceptable salt thereof.

* * * * *